United States Patent [19]

Theodoridis

[11] Patent Number: 5,399,543
[45] Date of Patent: Mar. 21, 1995

[54] 3-[4-(PHENYLMETHOXY)PHENYL]-1-SUB-STITUTED-6-HALOALKYL-URACIL HERBICIDES

[75] Inventor: George Theodoridis, Princeton, N.J.

[73] Assignee: FMC Corporation, Philadelphia, Pa.

[21] Appl. No.: 50,954

[22] Filed: Apr. 21, 1993

[51] Int. Cl.$^6$ ............... A01N 43/54; C07D 239/55
[52] U.S. Cl. .................... 504/243; 544/309; 544/311; 544/312; 544/314
[58] Field of Search ............ 544/309, 314, 311, 312; 504/243

[56] References Cited

U.S. PATENT DOCUMENTS

| | | | |
|---|---|---|---|
| 4,746,352 | 5/1988 | Wenger et al. | 504/243 |
| 4,812,164 | 3/1989 | Wenger et al. | 504/243 |
| 4,859,229 | 8/1989 | Wenger et al. | 504/243 |
| 4,927,451 | 5/1990 | Brouwer et al. | 504/243 |
| 4,941,909 | 7/1990 | Wenger et al. | 504/243 |
| 4,979,982 | 12/1990 | Brouwer et al. | 504/243 |
| 5,017,211 | 5/1991 | Wenger et al. | 504/243 |
| 5,019,151 | 5/1991 | Wada et al. | 504/243 |
| 5,022,915 | 6/1991 | Prisbylla | 504/243 |
| 5,041,156 | 8/1991 | Suchy et al. | 504/243 |
| 5,134,144 | 7/1992 | Brouwer et al. | 544/314 |
| 5,169,430 | 12/1992 | Strunk et al. | 544/310 |

FOREIGN PATENT DOCUMENTS 39272 2/1993 Japan .

OTHER PUBLICATIONS

STN International Registry File Search Results, pp. 3, 4, 6, 12; Chem. Abs. Accession No. CA118(7):59721u; Japan Kokai No. JP 4178373 (25 Jun. 1992).
Derwent Accession No. 44794T–C–Netherlands published application NL-7117690 (27 Jun. 1972).
Derwent Accession No. 56096a/31–Japan Published Application No. J5 3073-557 (30 Jun. 1978).
Derwent Accession No. 64714U–C–Japan Published Application No. JA–4852758Q Published 24 Jul. 1973.
Derwent Accession No. 61972V/35–Japan Published Application No. J48 103-736 Published 26 Dec. 1973.
Derwent Accession No. 35440V/19–Japan Published Application No. J49 024-952 (5 Mar. 1974).
Derwent Accession No. 22940B/12–Japan Published Application No. J5 4019-965 (15 Feb. 1979).
Derwent Accession No. 61975V/33–Japan Published Application No. J4 9000-432 published (5 Jan. 1974).
STN International Registry File Search Results p. 63–Chem Abstracts Accession No. CA89 (13):108753z Neth Appl. 7710554 (3 Apr. 1978).
STN International Registry File Search Results, p. 65–Chem Abstracts Accession No. CA93(5):46672u; Great Britian 1503244 (8 Mar. 1978).
STN International Registry File Search Results, pp. 63, 65, 97–Chem Abstracts Accession No. CA93(5):39503m; Japan Kokai No. JP 55031051 (5 Mar. 1980).

*Primary Examiner*—Cecilia Tsang
*Attorney, Agent, or Firm*—H. Robinson Ertelt; Robert M. Kennedy; Robert L. Andersen

[57] ABSTRACT

The present application discloses herbicidal 3-[4-(phenylmethoxy)phenyl]-1-substituted-6-haloalkyluracils of the formula

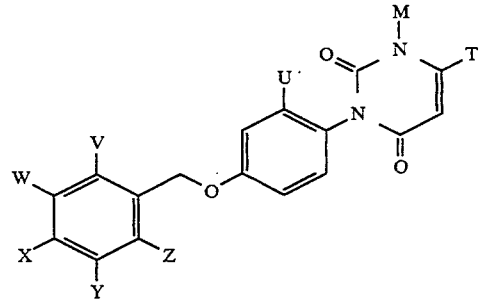

in which M is lower alkyl, lower 2-alkenyl, lower 2-alkynyl, lower alkoxymethyl or lower haloalkyl; T is lower haloalkyl; and U, V, W, X, Y, and Z are independently hydrogen, halogen, lower alkyl, lower haloalkyl, lower alkoxy, lower haloalkoxy, cyano or nitro; compositions thereof and use thereof to control unwanted plant growth.

21 Claims, No Drawings

3-[4-(PHENYLMETHOXY)PHENYL]-1-SUB-STITUTED-6-HALOALKYL-URACIL HERBICIDES

The invention described in this application pertains to weed control in agriculture, horticulture and other fields where there is a desire to control unwanted plant growth. More specifically, the present application describes certain herbioidal 3-[4-(phenylmethoxy)phenyl]-1-substituted-6-haloalkyluracils, compositions of them, methods of preparing them, and methods for preventing or destroying undesired plant growth by preemergence or postemergence application of the herbicidal compositions to the locus where control is desired. The present compounds may be used to effectively control a variety of grassy and broad leaf plant species, and are particularly efficacious for the postemergent control of broad leaf weeds. The present invention is particularly useful in agriculture; as a number of the compounds described show a selectivity favorable to certain crops such as wheat and corn at application levels which inhibit the growth of, or destroy a variety of weeds.

The herbicidal uracil derivatives of this invention are represented by the following structural formula

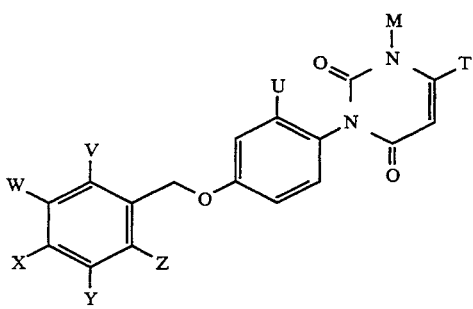

in which

M is lower alkyl (for example methyl, ethyl, propyl, isopropyl, or butyl), lower 2-alkenyl (for example, allyl), lower 2-alkynyl (for example, propargyl), lower alkoxymethyl (for example, methoxymethyl or isopropoxymethyl), or lower haloalkyl (for example, —CH$_2$Cl, —CF$_3$, or —CH$_2$CH$_2$F);

T is lower haloalkyl (for example, —CH$_2$Cl, —CF$_3$ or —CH$_2$CH$_2$F); and

U, V, W, X, Y, and Z are independently hydrogen, halogen (such as chlorine, fluorine, or bromine), lower alkyl (for example, methyl, ethyl, propyl, isopropyl, or butyl), lower haloalkyl (for example, —CH$_2$Cl, —CF$_3$, or —CH$_2$CH$_2$F), lower alkoxy (for example, methoxy or isopropoxy), lower haloalkoxy (for example, —OCH$_2$Cl, —OCF$_3$, or —OCH$_2$CH$_2$F), cyano or nitro.

Representative herbicidal compounds of this invention are listed in Table 1.

Preferred compounds include those in which M is methyl; T is trifluoromethyl; U is fluorine or hydrogen; and X is chlorine or fluorine, and V, W, Y, and Z are hydrogen; or one of V, W, or X is methoxy, and the other four substituents on the phenyl ring of the phenylmethyl moiety are hydrogen. Compounds in which U is fluorine or hydrogen, X is fluorine or preferably chlorine, and V, W, Y, and Z are hydrogen are particularly preferred. The most preferred compounds include 3-[4-(4-chlorophenylmethoxy)-2-fluorophenyl]-1-methyl-6-trifluoromethyl-uracil and 3-[4-(4-chlorophenylmethoxy)phenyl]-1-methyl-6-trifluoromethyluracil.

In each aspect of this invention the terms lower alkyl, lower alkoxy, lower haloalkyl, and lower haloalkoxy include straight or branched chains having 1-6 carbon atoms, preferably 1-4 carbon atoms. The terms lower alkenyl and lower alkynyl include straight or branched chains of 3-6 carbon atoms, preferably 3 or 4 carbon atoms. The hydrocarbon moiety of any lower haloalkyl or lower haloalkoxy radical is substituted with one or more of the same or different halogen atoms. Halo and halogen include fluorine, chlorine, and bromine.

Using commercially available starting materials or those whose syntheses would be known in the art, the compounds of this invention may be prepared using methods described in the following Examples and Schemata, or by using modifications thereof which would be within the skill of the art.

Many of the compounds of this invention may be prepared according to the following reaction schemata.

SCHEMA 1

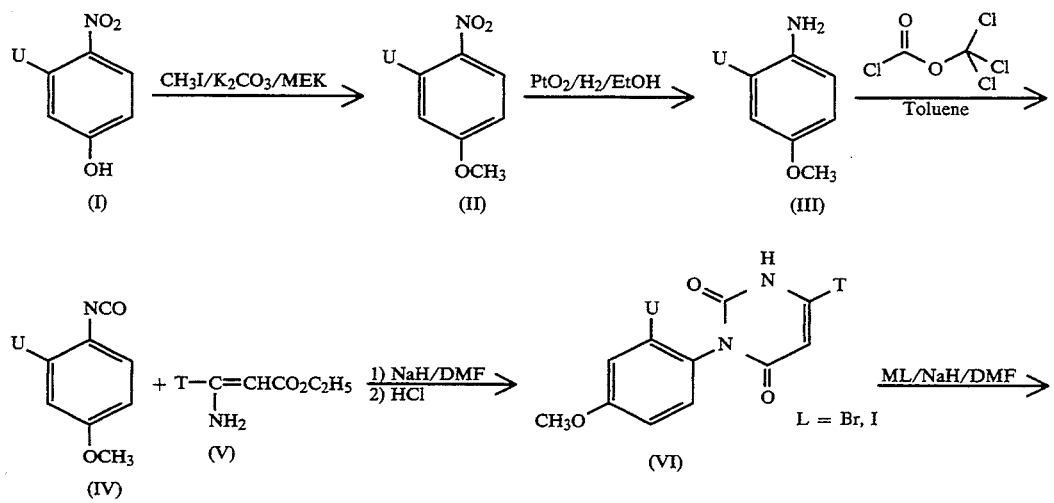

-continued
SCHEMA 1
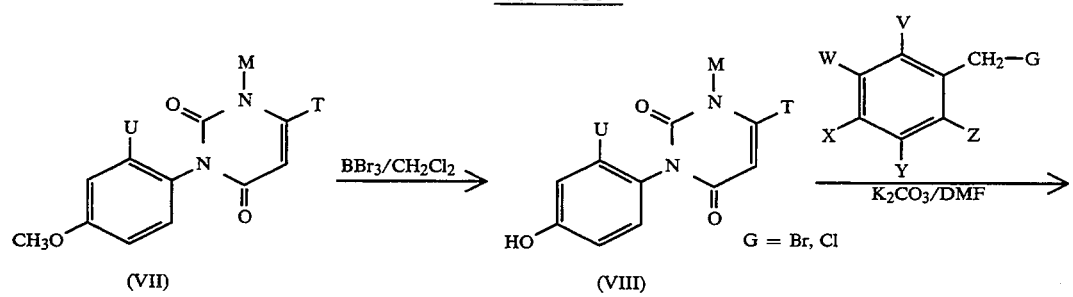
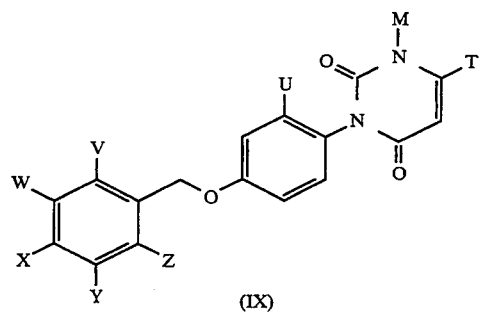
SCHEMA 2
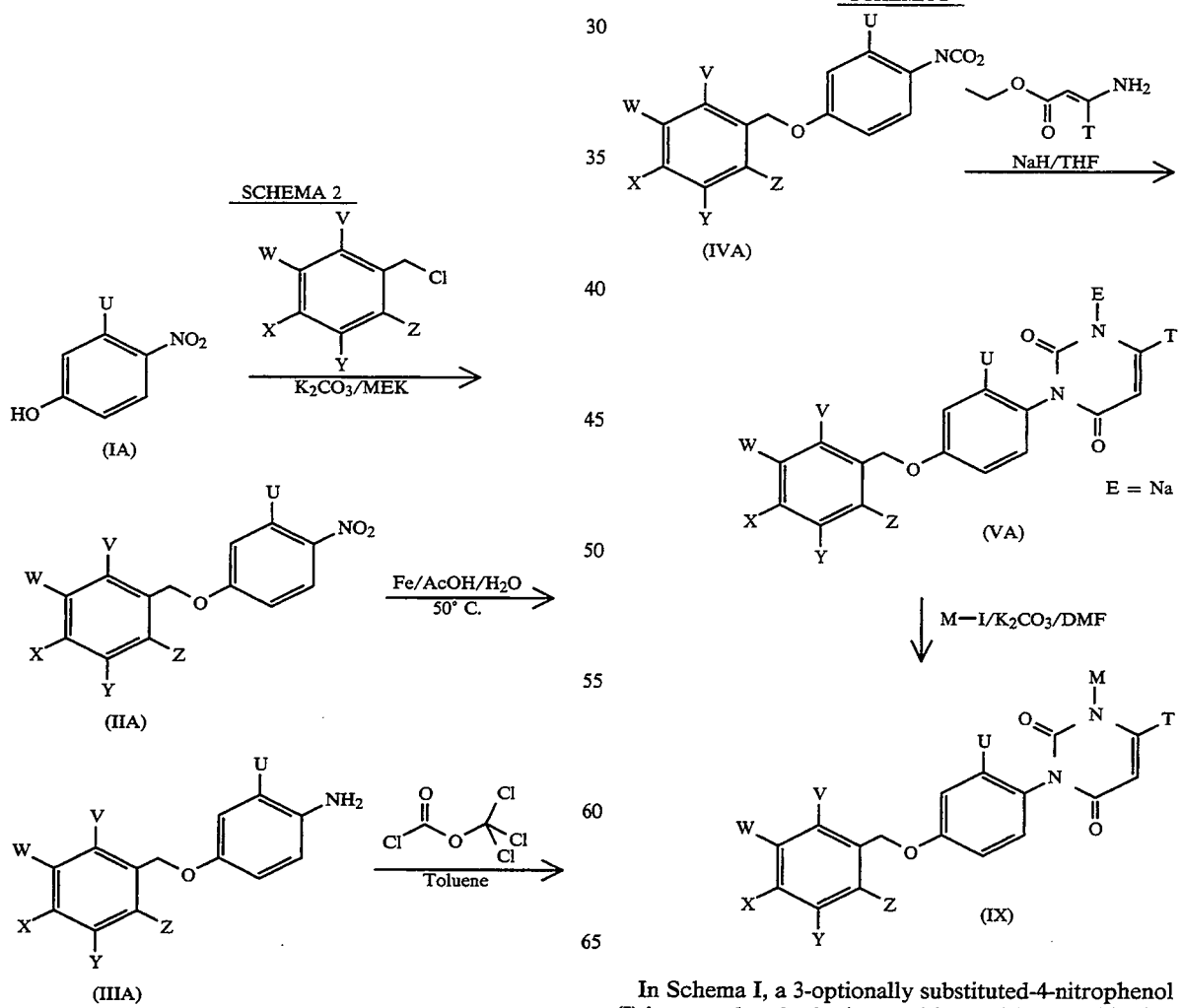
In Schema I, a 3-optionally substituted-4-nitrophenol (I) is reacted under basic conditions with methyl iodide in methyl ethyl ketone to give the corresponding 2-optionally substituted -4-methoxynitrobenzene (II). The nitrobenzene is in turn hydrogenated using a platinum oxide catalyst in ethanol to give the 2-optionally substituted-4-methoxyaniline (III), which is then treated with trichloromethyl chloroformate in toluene to give the corresponding 2-optionally substituted-4-methoxyphenyl isocyanate (IV). An ethyl 3-amino-3-lower haloalkylpropenoate (V) is treated with sodium hydride in N,N-dimethylformamide, and then with 2-optionally substituted-4-methoxyphenyl isocyanate, after which the reaction mixture is added to aqueous hydrochloric acid to give the 3-(4-methoxy-2-optionally substituted phenyl)-6-lower haloalkyluracil (VI). The uracil (VI) is alkylated, either after purification or in situ, by treatment with a lower alkyl bromide or iodide and sodium hydride in N,N-dimethylformamide to give 3-(4-methoxy-2-optionally substituted phenyl)-1-lower alkyl-6-lower haloalkyluracil (VII). The methoxy group of this compound is then dealkylated by treatment with boron tribromide in methylene chloride to give the corresponding 3-(4-hydroxy-2-optionally substituted phenyl)-1-lower alkyl-6-lower haloalkyluracil (VIII) which in turn is reacted with an optionally substituted phenylmethyl bromide or chloride and potassium carbonate in N,N-dimethylformamide to give the desired 3-[4-(optionally substituted phenylmethoxy)-1-optionally substituted phenyl]-1-lower alkyl-6-lower haloalkyluracil (IX).

In Schema 2, a 3-optionally substituted-4-nitrophenol (IA) is reacted under basic conditions with an optionally substituted phenylmethyl chloride in methyl ethyl ketone to give the corresponding 2-optionally substituted-4-(optionally substituted-phenylmethoxy)nitrobenzene (IIA). The nitrobenzene (IIA) is in turn reduced with iron powder in acetic acid and water to give the corresponding 2-optionally substituted-4-(optionally substituted-phenylmethoxy)aniline (IIIA), which is then treated with trichloromethyl chloroformate in toluene to give the corresponding 2-optionally substituted-4-(optionally substituted-phenylmethoxy)phenyl isocyanate (IVA). The phenyl isocyanate (IVA) is treated with sodium hydride in tetrahydrofuran, cyclized with an ethyl 3-amino-3-lower haloalkyl-2-propenoate, then alkylated with a lower alkyl halide in N, N-dimethylformamide to give the desired 3-[4-(optionally substituted-phenylmethoxy)-1-optionally substituted phenyl]-1-lower alkyl-6-lower haloalkyluracil (IX).

As is illustrated in Schema 1, certain lower alkoxy and hydroxy phenyl uracils are particularly useful for preparing the 3-[4-(phenylmethoxy)phenyl]-1-substituted -6-haloalkyluracil herbicides of this invention. These lower alkoxy and hydroxy phenyluracils include compounds VI, VII, and VIII illustrated in Schema 1, and are represented by the structural formula

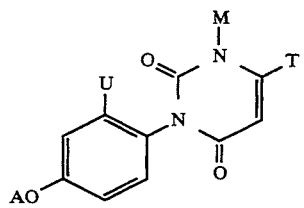

in which A is hydrogen or lower alkyl (for example methyl, ethyl, propyl, isopropyl, or butyl); M, T, and U are as defined above; and additionally, M may optionally be hydrogen when A is other than hydrogen.

Preferred embodiments include those compounds in which M is methyl; T is trifluoromethyl; and U is fluorine or hydrogen.

These compounds may be prepared as illustrated in Schema 1, or by using modifications thereof which would be within the skill of the art. For example, a $C_2$ or greater lower alkyl iodide may be substituted for methyl iodide in the formation of compound II, which when carried through Schema 1 will give the corresponding alkoxy analogues of compounds VI and VII.

As is illustrated in Schema 2, certain phenylmethoxyphenylisocyanates and 3-[4-(phenylmethoxy)phenyl]-6-haloalkyluracils are also useful in preparing the 3-[4-(phenylmethoxy)phenyl]-1-substituted-6-haloalkyluracil herbicides of this invention. Examples of these compounds are represented by formulae IVA and VA, respectively, in Schema 2. Additionally, 3-[4-(phenylmethoxy)phenyl]-6-haloalkyluracils in which E is hydrogen, potassium or ammonium instead of the preferred sodium may also be used in the last step of Schema 2 to prepare the compounds of this invention. Preferred imbodiments include those compounds having substituent arrangements of the preferred 3-[4-(phenylmethoxy)phenyl]-1-substituted-6-haloalkyluracil herbicides.

The phenylmethoxyphenylisocyanates and 3-[4-(phenylmethoxy)phenyl]-6-haloalkyluracils may be prepared as illustrated in Schema 2 and Examples 2 and 4, or by using modifications thereof which would be known in the art. For example, Compound VA may be acidified with, for example, dilute hydrochloric acid to obtain 3-[4-(phenylmethoxy)phenyl]-6-haloalkyluracils, i.e., Compound VA in which E is hydrogen. This compound may then be isolated using standard techniques known in the art. Treatment of this compound with, for example, an aqueous solution of ammonia or a potassium containing base such as potassium hydroxide or carbonate will produce the corresponding compounds in which E is ammonium or potassium.

Methods of preparing the compounds of this invention are further illustrated in the following nonlimiting examples.

EXAMPLE 1

SYNTHESIS OF
3-[4-(4-CHLOROPHENYLMETHOXY)-2FLUOROPHENYL]-1-METHYL-6-TRIFLUOROMETHYLURACIL

Step A 2-Fluoro-4-methoxynitrobenzene

A stirred solution of 10.6 grams (0.068 mole) of 3-fluoro-4-nitrophenol, 12.0 grams (0.084 mole) of methyl iodide and 18.6 grams (0.135 mole) of potassium carbonate in 150 mL of 2-butanone was heated at 70° C. for about 18 hours. After this time, the reaction mixture was filtered and concentrated under reduced pressure to a residue. The residue was dissolved in diethyl ether, and the solution was washed with water. The organic layer was dried with magnesium sulfate and filtered. The filtrate was concentrated under reduced pressure, yielding 11.4 grams of 2-fluoro-4-methoxynitrobenzene. The NMR spectrum was consistent with the proposed structure.

Step B 2-Fluoro-4-methoxyaniline

A mixture of 11.4 grams (0.067 mole) of 2-fluoro-4-methoxynitrobenzene and 0.4 gram of platinum oxide catalyst in 100 mL of ethanol was placed in a hydrogenation bottle and hydrogenated at 50 psi using a Parr hydrogenator. The completion of the hydrogenation required about two hours. After this time the reaction mixture was filtered to remove the catalyst. The filtrate was concentrated under reduced pressure, yielding 8.8 grams of 2-fluoro-4-methoxyaniline. The NMR spectrum was consistent with the proposed structure.

Step C 2-Fluoro-4-methoxyphenyl isocyanate

A solution of 8.8 grams (0.062 mole) of 2-fluoro-4-methoxyaniline in 70 mL of toluene was stirred, and a solution of 12.3 grams (0.062 mole) of trichloromethyl chloroformate in 30 mL of toluene was added dropwise. Upon completion of addition, the reaction mixture was warmed to reflux, where it was stirred for about 18 hours. After this time the reaction mixture was cooled and concentrated under reduced pressure, yielding about 10.4 grams of 2-fluoro-4-methoxyphenyl isocyanate. The product was used immediately in the next reaction.

Step D 3-(2-Fluoro-4-methoxyphenyl)-6-trifluoromethyluracil

A stirred mixture of 2.5 grams (0.062 mole) of sodium hydride (60% in mineral oil) in 50 mL of N,N-dimethylformamide was cooled to 0° C., and a solution of 11.2 grams (0.062 mole) of ethyl 3-amino-4,4,4-trifluorocrotonate in 50 mL of N,N-dimethylformamide was added dropwise. Upon completion of addition, the reaction mixture was stirred at 0° C. during a 30 minute period. After this time the reaction mixture was cooled in a dry ice-acetone bath, and a solution of 10.4 grams of 2-fluoro-4-methoxyphenyl isocyanate in 50 mL of N,N-dimethylformamide was added dropwise. Upon completion of addition, the reaction mixture was maintained at the dry ice-acetone bath temperature for one hour. After this time the reaction mixture was allowed to warm to ambient temperature, where it was stirred for about 18 hours. The reaction mixture was then poured into an aqueous 0.25N hydrochloric acid solution. The mixture was extracted with diethyl ether, and the extract was washed with water. The diethyl ether extract was in turn extracted with aqueous 1M sodium bicarbonate, and this extract was washed with diethyl ether. The sodium bicarbonate extract was then made acidic with concentrated hydrochloric acid, and it was in turn extracted with diethyl ether. The diethyl ether extract was washed with water and dried with magnesium sulfate. The mixture was filtered, and the filtrate was concentrated under reduced pressure, yielding 5.5 grams of 3-(2-fluoro-4-methoxyphenyl)-6-trifluoromethyluracil. The NMR spectrum was consistent with the proposed structure.

Step E 3-(2-Fluoro-4-methoxyphenyl)-1-methyl-6-trifluoromethyluracil

A mixture of 0.7 gram (0.017 mole) of sodium hydride (60% in mineral oil) in 30 mL of N,N-dimethylformamide was stirred, and a solution of 5.1 grams (0.017 mole) of 3-(2-fluoro-4-methoxyphenyl)-6-trifluoromethyluracil in 35 mL of N,N-dimethylformamide was added dropwise. The reaction mixture was then stirred for about 30 minutes, and a solution of 3.8 grams (0.017 mole) of methyl iodide in 35 mL of N,N-dimethylformamide was added dropwise. Upon completion of addition, the reaction mixture was stirred at ambient temperature for about 18 hours. After this time the reaction mixture was poured into an aqueous solution of 0.25N hydrochloric acid, and the mixture was extracted with diethyl ether. The ether extract was washed with an aqueous solution of 0.25N hydrochloric acid, water, and then with an aqueous solution saturated with sodium chloride. The organic layer was concentrated under reduced pressure to a residue. The residue was subjected to column chromatography on silica gel. Elution was accomplished using 1:1 ethyl acetate in heptane. The product-containing fractions were combined and concentrated under reduced pressure, yielding 3.9 grams of 3-(2-fluoro-4-methoxyphenyl)-1-methyl-6-trifluoromethyluracil. The NMR spectrum was consistent with the proposed structure.

Step F 3-(2-Fluoro-4-hydroxyphenyl)-1-methyl-6-trifluoromethyluracil

A solution of 32.9 mL (0.033 mole) of boron tribromide (1M in methylene chloride) in 50 mL of methylene chloride was stirred, and a solution of 3.5 grams (0.011 mole) of 3-(2-fluoro-4-methoxyphenyl)-1-methyl-6-trifluoromethyluracil in 50 mL of methylene chloride was added dropwise. Upon completion of addition, the reaction mixture was stirred at ambient temperature for about 18 hours. After this time the reaction mixture was poured into water. The organic layer was separated and the aqueous layer was extracted with methylene chloride. The methylene chloride extract and the organic layer were combined and washed with water. The organic layer was dried with magnesium sulfate and filtered. The filtrate was conc-entrated under reduced pressure, yielding about 2.9 grams of 3-(2-fluoro-4-hydroxyphenyl)-1-methyl-6-trifluoromethyluracil, mp 185°–190° C. The NMR spectrum was consistent with the proposed structure.

Step G 3-[4-(4-Chlorophenylmethoxy)-2-fluorophenyl]-1-methyl-6-trifluoromethyluracil A stirred solution of 0.6 gram (0.002 mole) of 3-(2-fluoro-4-hydroxyphenyl)-1-methyl-6-trifluoromethyluracil, 0.3 gram (0.002 mole) of 4-chlorophenylmethyl chloride, and 0.5 gram (0.004 mole) of potassium carbonate in 50 mL of N,N-dimethylformamide was heated at 80° C. for about 18 hours. After this time the reaction mixture was poured into aqueous 0.25N hydrochloric acid. The mixture was extracted with ethyl acetate, and the combined extracts were washed with water. The organic layer was dried with magnesium sulfate, and the mixture was filtered. The filtrate was then subjected to column chromatography on silica gel. Elution was accomplished using 1:4 heptane in ethyl acetate. The product-containing fractions were combined and concentrated under reduced pressure, yielding 0.7 gram of 3-[4-(4-chlorophenylmethoxy)-2-fluorophenyl]-1-methyl-6-trifluoromethyluracil, mp 134°–135° C. The NMR spectrum was consistent with the proposed structure.

EXAMPLE 2

SYNTHESIS OF 3-[4-(4-CHLOROPHENYLMETHOXY)-2-FLUOROPHENYL]-1-METHYL-6-TRIFLUOROMETHYLURACIL

Step A 2-Fluoro-4-(4-chlorophenylmethoxy)nitrobenzene

A stirred mixture of 7.8 grams (0.05 mole) of 3-fluoro-4-nitrophenol, 8.1 grams (0.05 mole) of 4-chlorophenylmethyl chloride and 6.9 grams (0.06 mole) of potassium carbonate in 80 mL of methyl ethyl ketone was heated at reflux for about 18 hours. After this time the reaction mixture was cooled to ambient temperature and filtered. The filtrate was concentrated under reduced pressure to a residue. The residue was subjected to column chromatography using silica gel. Elution was accomplished using methylene chloride. The product-containing fractions were combined and concentrated under reduced pressure, yielding 10.0 grams of 2-fluoro-4-(4-chlorophenylmethoxy)nitrobenzene, mp 86°–88° C.

Step B 2-Fluoro-4-(4-chlorophenylmethoxy)aniline

A stirred solution of 9.0 grams (0.032 mole) of 2-fluoro-4-(4-chlorophenylmethoxy)nitrobenzene and 10 mL of water in 150 mL of glacial acetic acid was maintained at 50° C. while 9.0 grams of iron powder was slowly added. Upon completion of addition, the reaction mixture was cooled to 25° C. where it was stirred for about one hour. After this time the reaction mixture was filtered, and the filtrate was poured into water. The mixture was then extracted with ethyl acetate. The extract was dried with magnesium sulfate and filtered. The filtrate was concentrated under reduced pressure to a residue. The residue was subjected to column chromatography using silica gel. Elution was accomplished using methylene chloride. The product-containing fractions were combined and concentrated under reduced pressure, yielding 7.1 grams of 2-fluoro-4-(4-chlorophenylmethoxy)aniline, mp 73°–75° C. The NMR spectrum was consistent with the proposed structure.

Step C  2-Fluoro-4-(4-chlorophenylmethoxy)phenyl isocyanate

A solution of 5.0 grams (0.02 mole) of 2-fluoro-4-(4-chlorophenylmethoxy)aniline in 150 mL of toluene was stirred and a solution of 3.4 mL (0.02 mole) of trichloromethyl chloroformate in 20 mL of toluene was added slowly. Upon completion of addition, the reaction mixture was stirred at 25° C. for one hour. After this time the reaction mixture was warmed to reflux, where it was stirred for about 18 hours. The reaction mixture was then concentrated under reduced pressure, yielding 5.5 grams of 2-fluoro-4-(4-chlorophenylmethoxy)phenyl isocyanate.

Step D 3-[4-(4-Chlorophenylmethoxy)-2-fluorophenyl]-1-methyl-6-trifluoromethyluracil A stirred mixture of 3.8 grams (0.02 mole) of ethyl 3-amino-4,4,4-trifluoro-2-butenoate and 0.8 gram (0.02 mole) of sodium hydride in 60 mL of tetrahydrofuran was cooled to −20° C., and a solution of 5.5 grams (0.02 mole) of 2-fluoro-4-(4-chlorophenylmethoxy)phenyl isocyanate in 60 mL of tetrahydrofuran was added slowly. Upon completion of addition, the reaction mixture was allowed to warm to ambient temperature. The reaction mixture was then heated to 70° C. where it was stirred for about 18 hours. After this time the reaction mixture was cooled and concentrated under reduced pressure to a solid residue. The residue was slurried in diethyl ether and filtered to collect the solid sodium salt of 3-[4-(4-chlorophenylmethoxy)-2-fluorophenyl]-6-trifluoromethyluracil. The solid sodium salt was then taken up with 2.8 grams (0.2 mole) of potassium carbonate and 5.9 grams (0.04 mole) of methyl iodide in 80 mL of N,N-dimethylformamide, and the stirred mixture was heated at 70° C. for about 7 hours. After this time the reaction mixture was poured into water, and the resultant solid was collected by filtration, yielding, when dried, 4.5 grams of 3-[4-(4-chlorophenylmethoxy)-2-fluorophenyl]-1-methyl-6-trifluoromethyluracil, mp 134°–135° C. The NMR spectrum was consistent with the proposed structure.

EXAMPLE 3

SYNTHESIS OF 3-[4-(4-CHLOROPHENYLMETHOXY)PHENYL]-1-METHYL-6-TRIFLUOROMETHYLURACIL

Step A 3-(4-Methoxyphenyl)-1-methyl-6-trifluoromethyluracil

A stirred mixture of 2.0 grams (0.025 mole) of sodium hydride (60% in mineral oil) in 100 mL of tetrahydrofuran was cooled to −10° C., and 4.6 grams (0.025 mole) of ethyl 3-amino-4,4,4-trifluoromethylcrotonate was added slowly. Upon completion of addition, 3.4 grams (0.025 mole) of 4-methoxyphenyl isocyanate was added. Upon completion of addition, the reaction mixture was stirred at −10° C. for 30 minutes, and then it was warmed to 25° C. where it was stirred for one hour. The reaction mixture was then warmed to 70° C. where it was stirred for about 18 hours. After this time 7.1 grams (0.050 mole) of methyl iodide was added. Upon completion of addition, the reaction mixture was stirred at 80° C. for about seven hours. After this time the reaction mixture was filtered, and the filtrate was concentrated under reduced pressure to a residue. The residue was neutralized with concentrated hydrochloric acid, and then it was extracted with diethyl ether. The ether layer was extracted with an aqueous dilute solution of sodium bicarbonate. The ether layer was then concentrated under reduced pressure, yielding when dried, 2.8 grams of 3-(4-methoxyphenyl)-1-methyl-6-trifluoromethyluracil, mp 118°–119° C. The NMR spectrum was consistent with the proposed structure.

Step B 3-(4-Hydroxyphenyl)-1-methyl-6-trifluoromethyluracil

This compound was prepared in a manner analogous to that of Step F of Example 1, using 2.4 grams (0.008 mole) of 3-(4-methoxyphenyl)-1-methyl-6-trifluoromethyluracil and 24 mL (0.024 mole) of boron tribromide (1M in methylene chloride). The yield of 3-(4-hydroxyphenyl)-1-methyl-6-trifluoromethyluracil was 2.0 grams.

Step C 3-[4-(4-Chlorophenylmethoxy)phenyl]-1-methyl-6-trifluoromethyluracil

This compound was prepared in a manner analogous to that of Step G of Example 1, using 0.6 gram (0.002 mole) of 3-(4-hydroxyphenyl)-1-methyl-6-trifluoromethyluracil, 0.4 gram (0.003 mole) of 4-chlorophenylmethyl chloride, and 0.4 gram (0.003 mole) of potassium carbonate in about 25 mL of N,N-dimethylformamide. The yield of 3-[4-(4-chlorophenylmethoxy)phenyl]-1-methyl-6-trifluoromethyluracil was 0.7 gram, mp 167°–169° C. The NMR spectrum was consistent with the proposed structure.

EXAMPLE 4

SYNTHESIS OF 3-[4-(4-CHLOROPHENYLMETHOXY-2-FLUOROPHENYL]-6-TRIFLUOROMETHYLURACIL

Step A Sodium salt of 3-[4-(4-chlorophenylmethoxy)-2-fluorophenyl]-6-trifluoromethyluracil A stirred mixture of 3.8 grams (0.02 mole) of ethyl 3-amino-4,4,4-trifluoro-2-butenoate and 0.8 gram (0.02 mole) of sodium hydride in 60 mL of tetrahydrofuran is cooled to −20° C., and a solution of 5.5 grams (0.02 mole) of 2-fluoro-4-(4-chlorophenylmethoxy)phenyl isocyanate in 60 mL of tetrahydrofuran is added slowly. Upon completion of addition the reaction mixture is allowed to warm slowly to ambient temperature. The reaction mixture is then heated to 70° C. where it is stirred for about 18 hours. After this time the reaction mixture is cooled and concentrated under reduced pressure to a solid residue. The residue is slurried in diethyl ether and filtered to collect the solid sodium salt of 3-[4-(4-chlorophenylmethoxy)-2-fluorophenyl]-6-trifluoromethyluracil.

Step B 3-[4-(4-chlorophenylmethoxy)-2-fluorophenyl]-1-methyl-6-trifluoromethyluracil A solution of 8.2 grams (0.02 mole) of the solid sodium salt of 3-[4-(4-chlorophenylmethoxy-2-fluorophenyl]-6-trifluoromethyluracil in 80 mL of water is stirred, and 100 mL of aqueous 0.25N hydrochloric acid is added dropwise during a 30 minute period. After this time, the mixture is extracted with diethyl ether. The ether extract is washed with water and dried with magnesium sulfate. The mixture is filtered and the filtrate concentrated under reduced pressure, yielding 3-[4-(4-chlorophenylmethoxy-2-fluorophenyl]-6-trifluoromethyluracil. Subsequent treatment of this compound with potassium carbonate and methyl iodide as described in Example 2, Step D, will give 3-[4-(4-chlorophenylmethoxy)-2-fluorophenyl]-1-methyl-6-trifluoromethyluracil.

HERBICIDAL ACTIVITY

The 3-[4-(phenylmethoxy)phenyl]-1-substituted-6-haloalkyluracil herbicides of this invention were tested for pre- and postemergence herbicidal activity using a variety of crops and weeds. The test plants included soybean (*Glycine max* var. Williams), field corn (*Zea mays* var. Agway 425X), wheat (*Triticum aestivum* var. Wheaton), morningglory (*Ipomea lacunosa* or *Ipomea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium pensylvanicum*).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 8–12 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27 g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 900 | 3 | 42 | 45 |
| 300 | 1 | 44 | 45 |
| 90 | 0.3 | 35 | 45.3 |
| 30 | 0.1 | 45 | 45.1 |
| 9 | 0.03 | 45 | 45.03 |
| 3 | 0.01 | 45 | 45.01 |

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. At this coverage the application rates are those shown in the above table for the individual herbicidal solutions. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 17–21 days the plants were examined and the phytotoxicity data were recorded.

Herbicidal activity data at selected application rates are given for various compounds of this invention in Table 2 and Table 3. The test compounds are identified by numbers which correspond to those in Table 1.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
|---|---|---|---|
| Rating Percent Control | Description of Main Categories | Crop Description | Weed Description |
| 1 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and | Control some- |

-continued

| Herbicide Rating System | | | |
|---|---|---|---|
| Rating Percent Control | Description of Main Categories | Crop Description | Weed Description |
| | | stand loss | what less than satisfactory |
| 80 | | Crop nearly destroyed, a few survivors | Satisfactory to good weed control |
| 90 | | Only occassional live plants left | Very good to excellent control |
| 100 | Complete effect | Complete crop destruction | Complete weed destruction |

For herbicidal application, the 3-[4-(phenylmethoxy)-phenyl]-1-substituted-6-haloalkyluracils are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersants. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carder, and usually also contain a small amount of a wetting, dispersing or emulsifying agent to facilitate dispersion. For example, a useful wettable powder formulation contains 80.8 parts of the herbicidal compound, 17.9 parts of Palmetto clay, 1.0 part of sodium lignosulfonate, and 0.3 part of sulfonated aliphatic polyester as wetting agents. Frequently additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but am not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form by a propellant, such as carbon dioxide, propane or butane, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The 3-[4-(phenylmethoxy)phenyl]-1-substituted-6-haloalkyluracils of this invention may be formulated and/or applied with insecticides, fungicides, nematicides, plant growth regulators, fertilizers, or other agricultural chemicals and may be used as effective soil sterilants as well as selective herbicides in agriculture.

In applying an active compound of this invention, whether formulated alone or with other agricultural chemicals, an effective amount and concentration of the active compound is of course employed; the amount may be as low as, for example, about 4 to 300 g/ha to, preferably about 10 to 30 g/ha. For field use, where there are losses of herbicide, higher application rates (for example, four times the rates mentioned above) may be employed.

The 3-[4-(phenylmethoxy)phenyl]-1-substituted-6-uracils of this invention may be used in combination with other herbicides, for example they may be mixed with, say, an equal or larger amount of a known herbicide such as aryloxyalkanoic acid herbicides such as (2,4-dichlorophenoxy)acetic acid (2,4-D), (4-chloro-2-methylphenoxy)acetic acid (MCPA), (±)-2-(4-chloro-2-methylphenoxy)propanoic acid (MCPP); urea herbicides, such as N,N-dimethyl-N'-[4-(1-methylethyl)-phenyl]urea (isoproturon); imidazolinone herbicides, such as 2-[4,5-dihydro-4-methyl-4-(1-methylethyl)-5-oxo-1H-imidazol-2-yl]-3-pyridinecarboxylic acid (imazapyr), a reaction product comprising (±)-2-[4,5-dihydro-4-methyl-4-(1-methylethyl)-5-oxo-1H-imidazol-2-yl]-4-methylbenzoic acid and (±)-2-[4,5-dihydro-4-methyl-4-(1-methylethyl)-5-oxo-1H-imidazol-2-yl]-5-methylbenzoic acid (imazamethabenz), (±)-2-[4,5-dihydro-4-methyl-4-(1-methylethyl)-5-oxo-1H-imidazol-2-yl]-5-ethyl-3-pyridinecarboxylic acid (imazethapyr),and (±)-2-[4,5-dihydro-4-methyl-4-(1-methylethyl)-5-oxo-1H-imidazol-2-yl]-3-quinolinecarboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil);sulfonylurea herbicides, such as 2-[[[[(4-chloro-6-methoxy-2-pyrimidinyl)amino]carbonyl]amino]sulfonyl]benzoic acid (chlorimuron), 2-chloro-N-[[(4-methoxy-6-methyl-1,3,5-triazin-2-yl)amino]carbonyl]-benzenesulfonamide (chlorsulfuron),2-[[[[(4,6-dimethoxy-2-pyrimidinyl)amino]carbonyl]amino]sulfonyl]-methyl]benzoic acid (bensulfuron), 2-[[[[(4,6-dimethoxy-2-pyrimidinyl)amino]carbonyl]amino]-sulfonyl]-1-methyl-1H-pyrazol-4-carboxylic acid (pyrazosulfuron),3-[[[[(4-methoxy-6-methyl-1,3,5-triazin-2-yl)amino]carbonyl]amino ]sulfonyl]-2-thiophene-carboxylic acid (thifensulfuron), and 2-(2-chloroethoxy)-N-[[(-4-methoxy-6-methyl-1,3,5-triazin-2-yl)amino]carbonyl]benzenesulfonamide(triasulfuron); 2-(4-aryloxyphenoxy)alkanoic acid herbicides, such as (±)-2-[4-[(6-chloro-2-benzoxazolyl)oxy]phenoxy]propanoic acid (fenoxaprop), (±)-2-[4-[[5-(trifluoromethyl)-2-pyridinyl]oxy]phenoxy]propanoic acid (fluazifop), (±)-2-[4-(6-chloro-2-quinoxalinyl)oxy]phenoxy]-propanoic acid (quizalofop), and (±)-2-[-(2,4-dichlorophenoxy)phenoxy]propanoic acid (diclofop); benzothiadiazinone herbicides, such as 3-(1-methylethyl)-1H-2,1,3-benzothiadiazin-4(3H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

Herbicidal 3-[4-(benzyloxy)phenyl]-1-substituted-6-haloalkyluracils

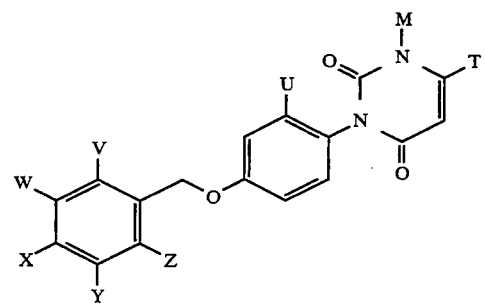

| Cmpd. No. | U | V | W | X | Y | Z | M | T |
|---|---|---|---|---|---|---|---|---|
| 1 | H | H | H | H | H | H | —CH$_3$ | —CF$_3$ |
| 2 | H | Cl | H | H | H | H | —CH$_3$ | —CF$_3$ |
| 3 | H | H | Cl | H | H | H | —CH$_3$ | —CF$_3$ |
| 4 | H | H | H | Cl | H | H | —CH$_3$ | —CF$_3$ |
| 5 | H | H | H | F | H | H | —CH$_3$ | —CF$_3$ |
| 6 | H | Cl | H | Cl | H | H | —CH$_3$ | —CF$_3$ |
| 7 | H | Cl | H | H | H | Cl | —CH$_3$ | —CF$_3$ |
| 8 | H | H | —OCH$_3$ | H | H | H | —CH$_3$ | —CF$_3$ |
| 9 | F | H | H | H | H | H | —CH$_3$ | —CF$_3$ |
| 10 | F | H | H | Cl | H | H | —CH$_3$ | —CF$_3$ |
| 11 | F | H | H | F | H | H | —CH$_3$ | —CF$_3$ |
| 12 | —CH$_3$ | H | H | H | H | H | —CH$_3$ | —CF$_3$ |
| 13 | —CH$_3$ | H | H | Cl | H | H | —CH$_3$ | —CF$_3$ |
| 14 | Cl | H | H | Cl | H | H | —CH$_3$ | —CF$_3$ |
| 15 | Br | H | H | Cl | H | H | —CH$_3$ | —CF$_3$ |
| 16 | F | H | H | —CF$_3$ | H | H | —CH$_3$ | —CF$_3$ |
| 17 | F | H | H | —OCH$_3$ | H | H | —CH$_3$ | —CF$_3$ |
| 18 | F | H | H | Br | H | H | —CH$_3$ | —CF$_3$ |

TABLE 1-continued

Herbicidal 3-[4-(benzyloxy)phenyl]-1-substituted-6-haloalkyluracils

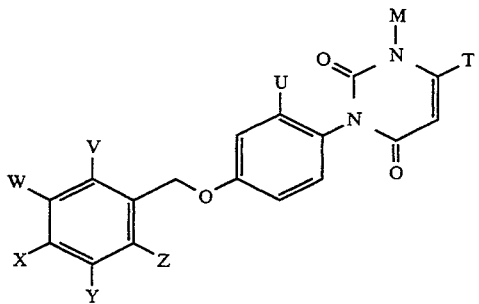

| Cmpd. No. | U | V | W | X | Y | Z | M | T |
|---|---|---|---|---|---|---|---|---|
| 19 | F | H | H | —CH₃ | H | H | —CH₃ | —CF₃ |
| 20 | F | H | H | —CH(CH₃)₂ | H | H | —CH₃ | —CF₃ |
| 21 | F | H | H | —OCF₂H | H | H | —CH₃ | —CF₃ |
| 22 | H | H | H | —CF₃ | H | H | —CH₃ | —CF₃ |
| 23 | H | H | H | Br | H | H | —CH₃ | —CF₃ |
| 24 | H | H | H | —CH₃ | H | H | —CH₃ | —CF₃ |
| 25 | H | H | H | —CN | H | H | —CH₃ | —CF₃ |
| 26 | H | H | H | —NO₂ | H | H | —CH₃ | —CF₃ |
| 27 | F | H | H | —CN | H | H | —CH₃ | —CF₃ |
| 28 | F | H | H | —NO₂ | H | H | —CH₃ | —CF₃ |
| 29 | H | H | —OCH₃ | H | —OCH₃ | H | —CH₂CF₂H | —CF₃ |
| 30 | H | H | H | H | H | H | —CHClCH₂Cl | —CF₃ |
| 31 | H | H | F | H | H | H | —C₂H₅ | —CF₃ |
| 32 | H | H | H | H | H | H | —CH(CH₃)₂ | —CH₂Cl |
| 33 | H | H | H | H | H | H | allyl | —CF₃ |
| 34 | H | H | H | H | H | H | propargyl | —CF₃ |
| 35 | H | H | H | H | H | H | —CH₂OC₂H₅ | —CF₃ |
| 36 | —CF₃ | H | H | H | H | H | —CH₃ | —CF₃ |
| 37 | —OC₂H₅ | H | H | H | H | H | —CH₃ | —CF₃ |
| 38 | —OCF₃ | H | H | H | H | H | —CH₃ | —CF₃ |
| 39 | Cl | H | H | H | H | H | —CH₃ | —CF₃ |
| 40 | H | —OCH₃ | H | H | H | H | —CH₃ | —CF₃ |
| 41 | H | H | Cl | Cl | H | H | —CH₃ | —CF₃ |
| 42 | H | Cl | Cl | H | H | H | —CH₃ | —CF₃ |
| 43 | H | H | Cl | H | Cl | H | —CH₃ | —CF₃ |
| 44 | H | H | H | —OCH₃ | H | H | —CH₃ | —CF₃ |

TABLE 2

PREEMERGENCE HERBICIDAL ACTIVITY (% CONTROL)

| Compound No. | 1 | 2 | 3 | 4 |
|---|---|---|---|---|
| Rate (kg/ha) | 0.3 | 0.3 | 0.3 | 0.3 |
| Species | | | | |
| Soybean | 75 | 20 | 10 | 60 |
| Wheat | 10 | 5 | 0 | 10 |
| Corn | 60 | 15 | 10 | 30 |
| Velvetleaf | 100 | 100 | 80 | 100 |
| Morningglory | 100 | 60 | 10 | 90 |
| Chickweed | 90 | 0 | 0 | 100 |
| Cocklebur | 75 | 10 | 0 | 30 |
| Blackgrass | 10 | 0 | 0 | 50 |
| Green foxtail | 100 | 100 | 95 | 100 |
| Johnsongrass | 75 | 70 | 20 | 95 |

| Compound No. | 5 | 6 | 7 | 8 |
|---|---|---|---|---|
| Rate (kg/ha) | 0.3 | 0.3 | 0.3 | 0.3 |
| Species | | | | |
| Soybean | 60 | 20 | 0 | 10 |
| Wheat | 20 | 0 | 0 | 15 |
| Corn | 50 | 10 | 0 | 35 |
| Velvetleaf | 100 | 100 | 0 | 100 |
| Morningglory | 100 | 45 | 0 | 65 |
| Chickweed | 100 | 10 | 0 | 90 |
| Cocklebur | 40 | 10 | 0 | 0 |
| Blackgrass | 20 | 0 | 0 | 10 |
| Green foxtail | 100 | 100 | 0 | 100 |
| Johnsongrass | 90 | 60 | 0 | 80 |

| Compound No. | 9 | 10 | 11 | 12 |
|---|---|---|---|---|
| Rate (kg/ha) | 0.3 | 0.3 | 0.3 | 0.3 |
| Species | | | | |
| Soybean | 85 | 100 | 85 | 10 |
| Wheat | 40 | 20 | 20 | 0 |
| Corn | 80 | 20 | 85 | 40 |
| Velvetleaf | 100 | 100 | 100 | 60 |
| Morningglory | 100 | 100 | 100 | 10 |
| Chickweed | 90 | 100 | 100 | 0 |
| Cocklebur | 50 | 100 | 90 | 0 |
| Blackgrass | 30 | 50 | 20 | 0 |
| Green foxtail | 100 | 100 | 100 | 80 |
| Johnsongrass | 100 | 95 | 95 | 60 |

| Compound No. | 13 | 22 | 40 | 41 |
|---|---|---|---|---|
| Rate (kg/ha) | 0.3 | 0.3 | 0.3 | 0.3 |
| Species | | | | |
| Soybean | 40 | 90 | 50 | 40 |
| Wheat | 0 | 0 | 20 | 0 |
| Corn | 30 | 30 | 75 | 0 |
| Velvetleaf | 100 | 100 | 100 | 100 |
| Morningglory | 60 | 90 | 100 | 80 |
| Chickweed | 10 | 100 | 80 | 95 |
| Cocklebur | 0 | 50 | 20 | 20 |
| Blackgrass | 30 | 15 | 30 | 20 |
| Green foxtail | 100 | 100 | 100 | 95 |
| Johnsongrass | 90 | 70 | 100 | 20 |

| Compound No. | 42 | 43 | 44 |
|---|---|---|---|
| Rate (kg/ha) | 0.3 | 0.3 | 0.3 |

TABLE 2-continued

PREEMERGENCE HERBICIDAL ACTIVITY
(% CONTROL)

| Species | | | |
|---|---|---|---|
| Soybean | 0 | 0 | 40 |
| Wheat | 0 | 0 | 10 |
| Corn | 0 | 0 | 0 |
| Velvetleaf | 80 | 0 | 100 |
| Morningglory | 70 | 0 | 100 |
| Chickweed | 0 | 0 | 20 |
| Cocklebur | 0 | 0 | 25 |
| Blackgrass | 0 | 0 | 20 |
| Green foxtail | 60 | 0 | 60 |
| Johnsongrass | 30 | 0 | 10 |

TABLE 3

POSTEMERGENCE HERBICIDAL ACTIVITY
(% CONTROL)

| Compound No. | 1 | 2 | 3 | 4 |
|---|---|---|---|---|
| Rate (kg/ha) | 0.3 | 0.3 | 0.3 | 0.3 |
| Species | | | | |
| Soybean | 80 | 60 | 45 | 95 |
| Wheat | 0 | 0 | 10 | 0 |
| Corn | 30 | 45 | 60 | 50 |
| Velvetleaf | 100 | 80 | 100 | 95 |
| Morningglory | 95 | 60 | 90 | 100 |
| Chickweed | 95 | 0 | 70 | 100 |
| Cocklebur | 80 | 30 | 100 | 100 |
| Blackgrass | 10 | 0 | 0 | 0 |
| Green foxtail | 90 | 85 | 95 | 80 |
| Johnsongrass | 60 | 10 | 90 | 0 |
| Compound No. | 5 | 6 | 7 | 8 |
| Rate (kg/ha) | 0.3 | 0.3 | 0.3 | 0.3 |
| Species | | | | |
| Soybean | 90 | 40 | 0 | 85 |
| Wheat | 0 | 0 | 0 | 10 |
| Corn | 75 | 20 | 0 | 85 |
| Velvetleaf | 100 | 80 | 0 | 100 |
| Morningglory | 100 | 50 | 10 | 100 |
| Chickweed | 100 | 0 | 0 | 100 |
| Cocklebur | 100 | 60 | 0 | 100 |
| Blackgrass | 30 | 0 | 0 | 10 |
| Green foxtail | 90 | 40 | 90 | 100 |
| Johnsongrass | 75 | 20 | 0 | 100 |
| Compound No. | 9 | 10 | 11 | 12 |
| Rate (kg/ha) | 0.3 | 0.3 | 0.3 | 0.3 |
| Species | | | | |
| Soybean | 70 | 95 | 80 | 20 |
| Wheat | 20 | 10 | 20 | 0 |
| Corn | 70 | 50 | 70 | 0 |
| Velvetleaf | 100 | 100 | 100 | 30 |
| Morningglory | 100 | 100 | 100 | 20 |
| Chickweed | 80 | 100 | 80 | 0 |
| Cocklebur | 100 | 100 | 100 | 0 |
| Blackgrass | 0 | 40 | 0 | 0 |
| Green foxtail | 100 | 100 | 100 | 50 |
| Johnsongrass | 95 | 95 | 100 | 0 |
| Compound No. | 13 | 22 | 40 | 41 |
| Rate (kg/ha) | 0.3 | 0.3 | 0.3 | 0.3 |
| Species | | | | |
| Soybean | 30 | 50 | 90 | 85 |
| Wheat | 0 | 20 | 20 | 0 |
| Corn | 40 | 20 | 50 | 25 |
| Velvetleaf | 100 | 40 | 100 | 100 |
| Morningglory | 100 | 95 | 90 | 100 |
| Chickweed | 30 | 15 | 15 | 85 |
| Cocklebur | 90 | 40 | 100 | 100 |
| Blackgrass | 20 | 30 | 10 | 0 |
| Green foxtail | 80 | 90 | 100 | 45 |
| Johnsongrass | 20 | 80 | 90 | 35 |
| Compound No. | 42 | 43 | 44 | |
| Rate (kg/ha) | 0.3 | 0.3 | 0.3 | |
| Species | | | | |
| Soybean | 25 | 10 | 40 | |

TABLE 3-continued

POSTEMERGENCE HERBICIDAL ACTIVITY
(% CONTROL)

| Wheat | 0 | 0 | 10 |
|---|---|---|---|
| Corn | 30 | 30 | 30 |
| Velvetleaf | 90 | 0 | 40 |
| Morningglory | — | 10 | 90 |
| Chickweed | 0 | 0 | 20 |
| Cocklebur | 35 | 0 | 50 |
| Blackgrass | 0 | 0 | 50 |
| Green foxtail | 50 | 0 | 70 |
| Johnsongrass | 50 | 30 | 50 |

I claim:
1. A compound of the formula

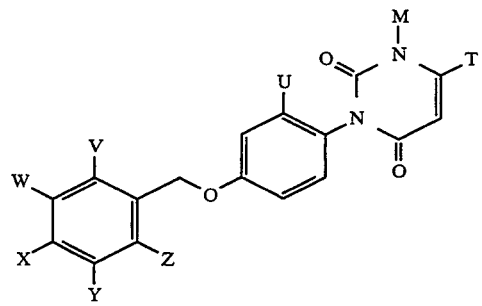

in which M is lower alkyl, lower 2-alkenyl, lower 2-alkynyl, lower alkoxymethyl or lower haloalkyl; T is lower haloalkyl; and U, V, W, X, Y and Z are independently hydrogen, halogen, lower alkyl, lower haloalkyl, lower alkoxy, lower haloalkoxy, cyano or nitro.

2. The compound of claim 1 in which T is lower fluoroalkyl.

3. The compound of claim 2 in which M is lower alkyl.

4. The compound of claim 3 in which T is trifluoromethyl.

5. The compound of claim 4 in which M is methyl.

6. The compound of claim 5 in which U, V, W, X, Y, and Z are independently hydrogen, halogen, or lower alkoxy.

7. The compound of claim 6 in which V, W, X, Y, and Z are hydrogen.

8. The compound of claim 7 in which U is fluorine, hydrogen, or chlorine.

9. The compound of claim 6 in which one of V, W, X, Y, or Z is halogen or lower alkoxy.

10. The compound of claim 9 in which U is hydrogen, chlorine or fluorine.

11. The compound of claim 10 in which V, W or X is lower alkoxy.

12. The compound of claim 11 in which V, W or X is methoxy.

13. The compound of claim 10 in which X is chlorine or fluorine.

14. The compound of claim 13 in which U is fluorine.

15. The compound of claim 1 in which the compound is 3-[4-(4chlorophenylmethoxy)phenyl]-1-methyl-6-trifluoromethyluracil.

16. The compound of claim 1 in which the compound is 3-[4-(4-chlorophenylmethoxy)-2-fluorophenyl]-1-methyl-6-trifluoromethyluracil.

17. A compound of the formula

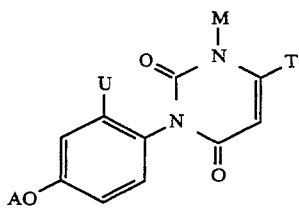

in which M is hydrogen, lower alkyl, lower 2-alkenyl, lower 2-alkynyl, lower alkoxymethyl, or lower haloalkyl; A is lower alkyl; T is lower haloalkyl; and U is hydrogen, halogen, lower alkyl, lower haloalkyl, lower alkoxy, lower haloalkoxy, cyano, or nitro; and with the proviso that when T is trifluoromethyl or M is hydrogen, U is other than hydrogen and A is other than methyl.

18. A compound of the formula

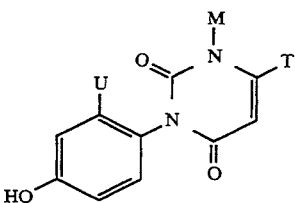

in which M is lower alkyl, lower 2-alkenyl, lower 2-alkynyl, lower alkoxymethyl, or lower haloalkyl; T is lower haloalkyl; and U is hydrogen, halogen, lower alkyl, lower haloalkyl, lower alkoxy, lower haloalkoxy, cyano, or nitro; and with the proviso that when T is trifluoromethyl, U is other than hydrogen.

19. A compound of the formula

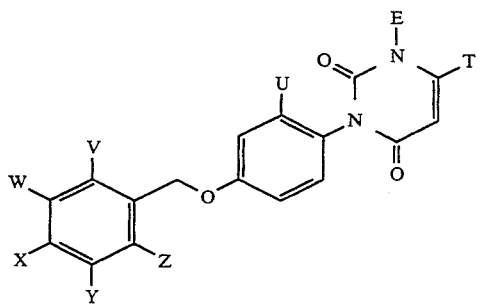

in which E is hydrogen, sodium, potassium, or ammonium; T is lower haloalkyl; and U, V, W, X, Y and Z are independently hydrogen, halogen, lower alkyl, lower haloalkyl, lower alkoxy, lower haloalkoxy, cyano, or nitro.

20. A composition comprising an herbicidally effective amount of the compound of claim 1 in admixture with a suitable carrier.

21. A method of controlling undesired plant growth which comprises applying to the locus where control is desired an herbicidally effective amount of the composition of claim 1.

* * * * *